United States Patent [19]

DeSatnick et al.

[11] Patent Number: 5,626,596

[45] Date of Patent: May 6, 1997

[54] TOOL SUPPORT ASSEMBLY WITH BIDIRECTIONAL POSITION CONTROL

[75] Inventors: Allen DeSatnick; Roger J. Simpson, both of Marblehead, Mass.

[73] Assignee: Questus Corporation, Marblehead, Mass.

[21] Appl. No.: 388,955

[22] Filed: Feb. 15, 1995

[51] Int. Cl.$^6$ ............................................. A61B 17/32
[52] U.S. Cl. ........................... 606/170; 606/167; 606/185; 128/754
[58] Field of Search .................. 606/1, 167, 170, 606/158, 185, 205–211; 128/750–755

[56] References Cited

U.S. PATENT DOCUMENTS

| | | |
|---|---|---|
| 4,491,132 | 1/1985 | Aikins. |
| 4,674,500 | 6/1987 | DeSatnick. |
| 4,733,662 | 3/1988 | DeSatnick et al.. |
| 4,848,338 | 7/1989 | DeSatnick et al.. |
| 4,962,770 | 10/1990 | Agee et al.. |
| 4,963,147 | 10/1990 | Agee et al.. |
| 4,994,079 | 2/1991 | Genese et al. .............. 606/206 |
| 5,089,000 | 2/1992 | Agee et al.. |
| 5,141,517 | 8/1992 | Shutt. |
| 5,195,533 | 3/1993 | Chin et al. .............. 128/751 |
| 5,306,284 | 4/1994 | Agee et al.. |
| 5,368,605 | 11/1994 | Miller, Jr. .............. 604/174 |

*Primary Examiner*—Michael Buiz
*Assistant Examiner*—William Lewis
*Attorney, Agent, or Firm*—Lappin & Kusmer LLP

[57] ABSTRACT

A tool support assembly having bi-directional position control. A tool support element is positioned within a housing and movable axially therealong in response to applied axial force F on a control element. A bi-directional positioning assembly links the tool support element to the housing and includes at least one detent element affixed to the housing and having at least one detent which extends transverse to the axis of the housing. The positioning assembly further includes at least one latch element captively positioned within the housing and selectively movable along the axis relative to the housing. The latch element includes at least one lock arm which is resiliently biasable toward one of the detents and is adapted for selective engagement therewith. A control element is captively positioned within the housing and is movable relative to the housing along the axis. When no force is applied to the control element relative to the housing, and when at least one of the lock arms is engaged with one of the detents, the tool support element is fixedly positioned relative to the housing. In response to a force to the control element applied in either axial direction relative to the housing, the lock arms disengage from the detents and permit the tool support element to move in the corresponding axial direction relative to the housing.

3 Claims, 4 Drawing Sheets

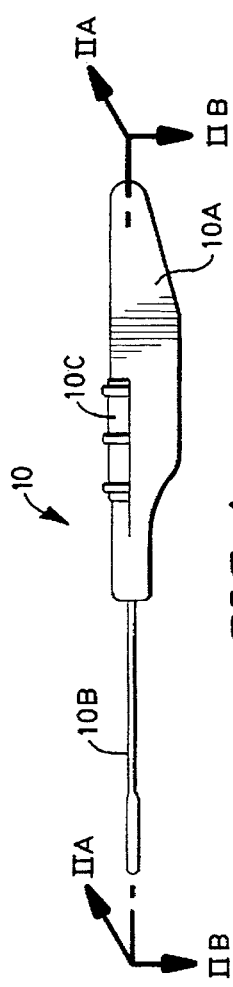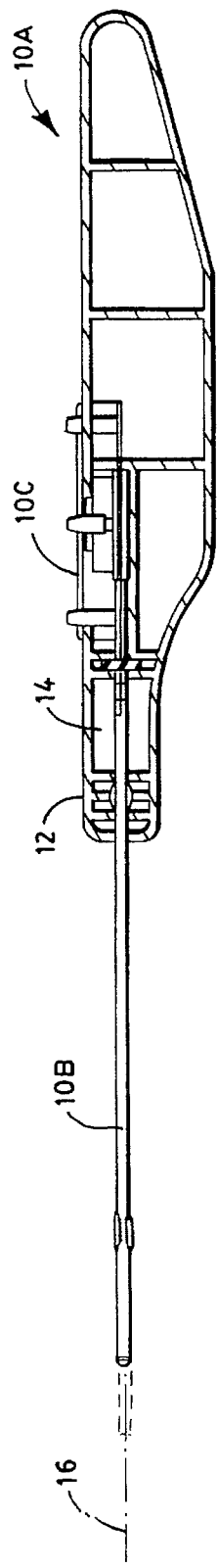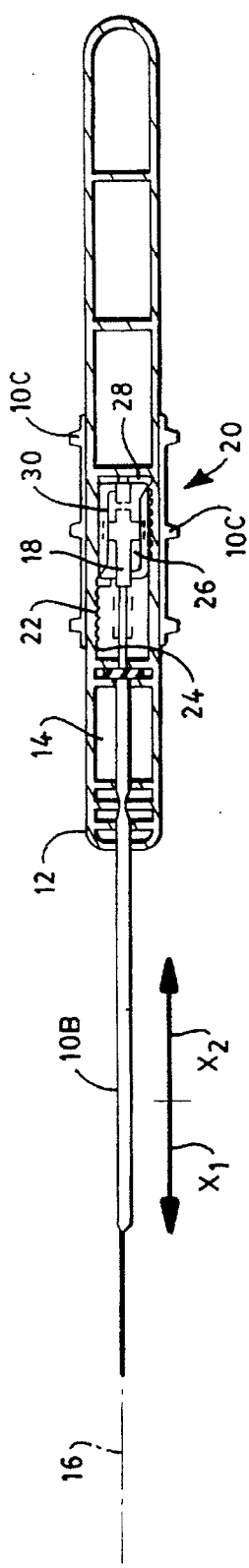

TOOL SUPPORT ASSEMBLY WITH BIDIRECTIONAL POSITION CONTROL

TECHNICAL FIELD

The present invention relates generally to retractable devices which have an operating element movable between two or more working positions. More particularly, the invention relates to retractable instruments, such as surgical instruments, which have an operating element which can be locked in any of several positions.

BACKGROUND OF THE INVENTION

U.S. Pat. No. 5,141,517 to Shutt discloses a retractable instrument having a locking mechanism which can be automatically actuated for selective positioning and locking of the instrument. The handle of the instrument includes several abutment elements which cooperatively engage with corresponding transverse bends in the end of an instrument support shaft within the handle. A slidable actuating pin moves the support shaft axially so that the support shall engages positively with one of the abutment elements, thereby locking the support shaft and preventing rearward axial motion of the instrument after it is locked in place.

U.S. Pat. No. 4,674,500 to DeSatnick discloses a sheathed knife instrument having a blade which is selectively movable by way of a sliding element on the handle. The sliding element is controlled by finger movement, thereby permitting single-handed operation of the knife instrument. The sliding element moves axially and can be rotated transverse to that axis to lock the knife blade in place.

Neither of the devices permits effective single-handed retractable operation of a surgical instrument, such as a surgical knife, with simple, bi-directional control.

It is therefore an object of the present invention to provide a tool support assembly having bi-direction position control and being operable with one hand.

It is an other object of the present invention to provide a surgical instrument having bi-directional instrument position control and means for selectively locking the surgical instrument in any number of positions with one hand.

SUMMARY OF THE INVENTION

These and other objects of the invention are achieved by the present invention which, in one aspect, provides a tool support assembly with a bi-direction position control. The tool support assembly comprises a housing which defines an interior channel extending along an axis, a tool support element positioned within the channel and movable axially in the channel, and a bi-directional positioning assembly which couples the tool support element and the housing. The bi-directional positioning assembly includes at least one detent element which is affixed to the housing. The detent element includes at least one detent which extends transverse to the axis and faces the channel. The bi-direction positioning assembly further includes at least one latch element which is captively positioned within the channel and which is selectively movable along the axis. The latch element includes at least one lock arm which is resiliently biasable toward the detent element and is shaped for selective engagement with at least one of the detents. The bi-directional positioning assembly further includes a control element which is captively positioned within the housing and movable relative to the housing along the axis. The latch element and the control element cooperate so that in response to substantially no force applied to the control element relative to the housing, and with at least one of the lock arms engaged with one of the detents, the tool support element is fixedly positioned relative to the housing. Further, in response to force applied to the control element relative to the housing in a first direction X1 along the axis, the lock arms disengage from the detents, thereby permitting the tool support element to move relative to the housing in the first direction X1.

The latch element and the control element further cooperate so that in response to a force applied to the control element relative to the housing in a second direction X2 along the axis, the second direction X2 being opposite to the first direction X1, the lock arms disengage from the detents, thereby permitted the tool support element to move relative to the housing in the second direction X2.

In one form of the invention, the bi-directional positioning assembly includes a first detent element on a first side of the channel, and a second detent element on a second side of the channel. The first and second sides of the channel oppose and face each other. Each of the first and second detent elements include a linear array of detents which extends along the axis and faces the interior of the channel.

The latch element includes first and second lock arms, each of which is resiliently biasable toward a corresponding detent element and shaped for selective engagement with one of the detents of the that detent element. The second lock arm is also resiliently biasable toward one of the detents of the second detent element and is shaped for selective engagement therewith.

The first lock arm includes an element which is operative in response to a force applied to the tool support element relative to the housing in a first axial direction X1 for interfering engagement with one of the detents of the first detent element to prevent motion of the tool support element relative to the housing in the first direction X1. The first lock arm further includes an element operative in response to a force applied to the tool support element relative to the housing in a second axial direction X2 opposite to direction X1 for disengaging the detents of the first detent element to permit motion of the tool support element relative to the housing in the second direction X2.

The second lock arm includes an element operative in response to a force applied to the tool support element relative to the housing in the second axial direction X2 for interfering engagement with one of the detents of the second detent element to prevent motion of the tool support element relative to the housing in the second direction X2. Similarly, the second lock arm further includes an element operative in response to a force applied to the tool support element relative to the housing in the first axial direction X1 for disengaging the detents of the second detent element to permit motion of the tool support element relative to the housing in the first axial direction X1.

These an other features of the invention will be more fully appreciated with reference to the following detailed description which is to be read in conjunction with the attached drawings.

BRIEF DESCRIPTION OF THE DRAWINGS

The invention is further described by the following description and figures, in which:

FIG. 1 is a side elevational view of a tool support assembly according to the present invention;

FIG. 2A is a side cross-sectional view of the tool support assembly of FIG. 1 taken along section lines IIA—IIA;

FIG. 2B is a plan cross-sectional view of the tool support assembly of FIG. 1 taken along section lines IIB—IIB;

Like elements in the respective Figures have the same reference numbers.

DESCRIPTION OF THE PREFERRED EMBODIMENT

The tool support assembly of the present invention is particularly useful with surgical instruments, such as retractable cutting instruments. A typical surgical instrument embodying the invention is shown in FIG. 1. The tool comprises a handle 10A and a tool, such as a blade 10B. A trigger element 10C is disposed on the handle and is adapted for sliding axial movement relative to the handle 10A in response to applied force from an operator's finger.

As shown in FIG. 2A, the handle 10A comprises a housing 12 which defines a hollow interior channel 14 extending generally along a longitudinal axis 16. The housing 12 is shaped for comfortable and convenient positioning within an operator's hand and can have a textured exterior surface for enhancing the operator's grip thereon. The hollow interior portion of the channel 14 permits the inclusion of weights or ballast to further enhance the operator's ability to comfortably hold and to controllably grip the instrument.

The tool support assembly 10 can be seen most clearly in FIG. 2B. The tool support assembly 10 is located within a portion of the housing 12 and beneath trigger element 10C. The operating element, such as blade 10B, extends longitudinally from the housing 12 along an axis 16 and is movable in a first axial direction X1 and a second axial direction X2 opposite to direction X1, as shown in FIG. 2B.

Figure 3A:
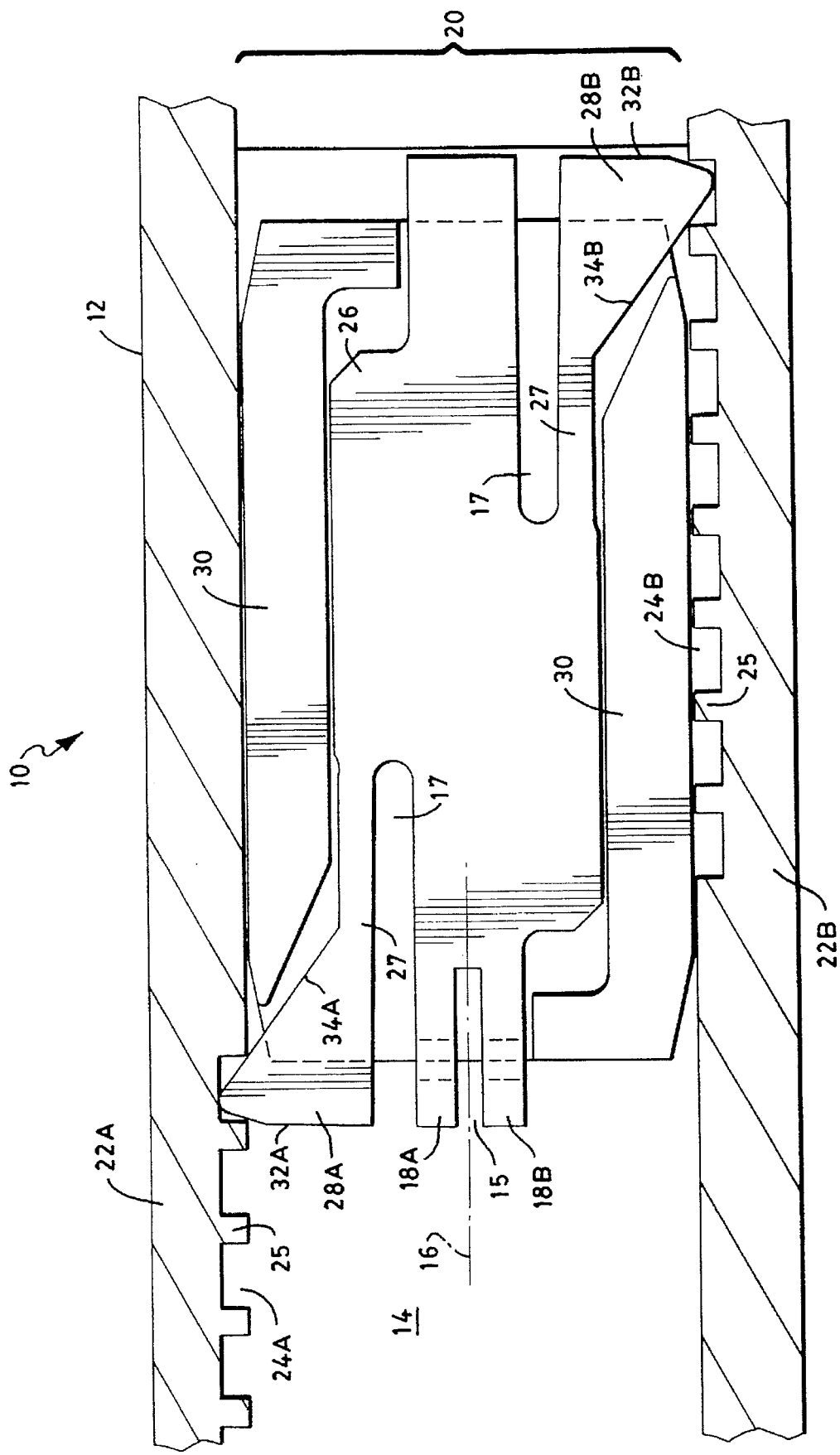
FIG. 3A is an enlarged detail cross-sectional view of the bi-directional positioning assembly shown in FIG. 2B.
Figure 3B:
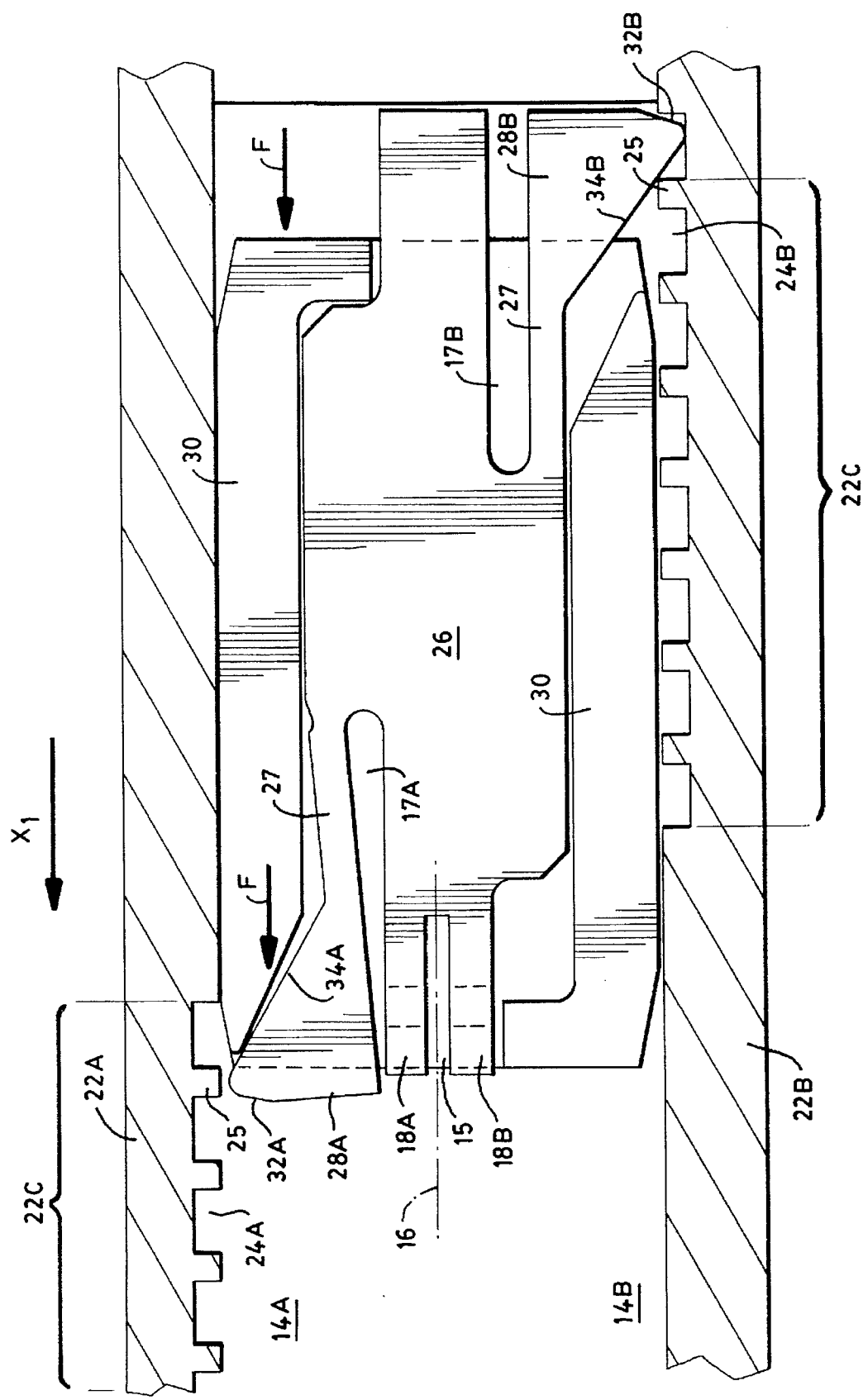
FIG. 3B is an enlarged detail cross-sectional view of the bi-directional positioning assembly shown in FIG. 3A, in which force is applied to the control element along an axial direction X1.
Figure 3C:
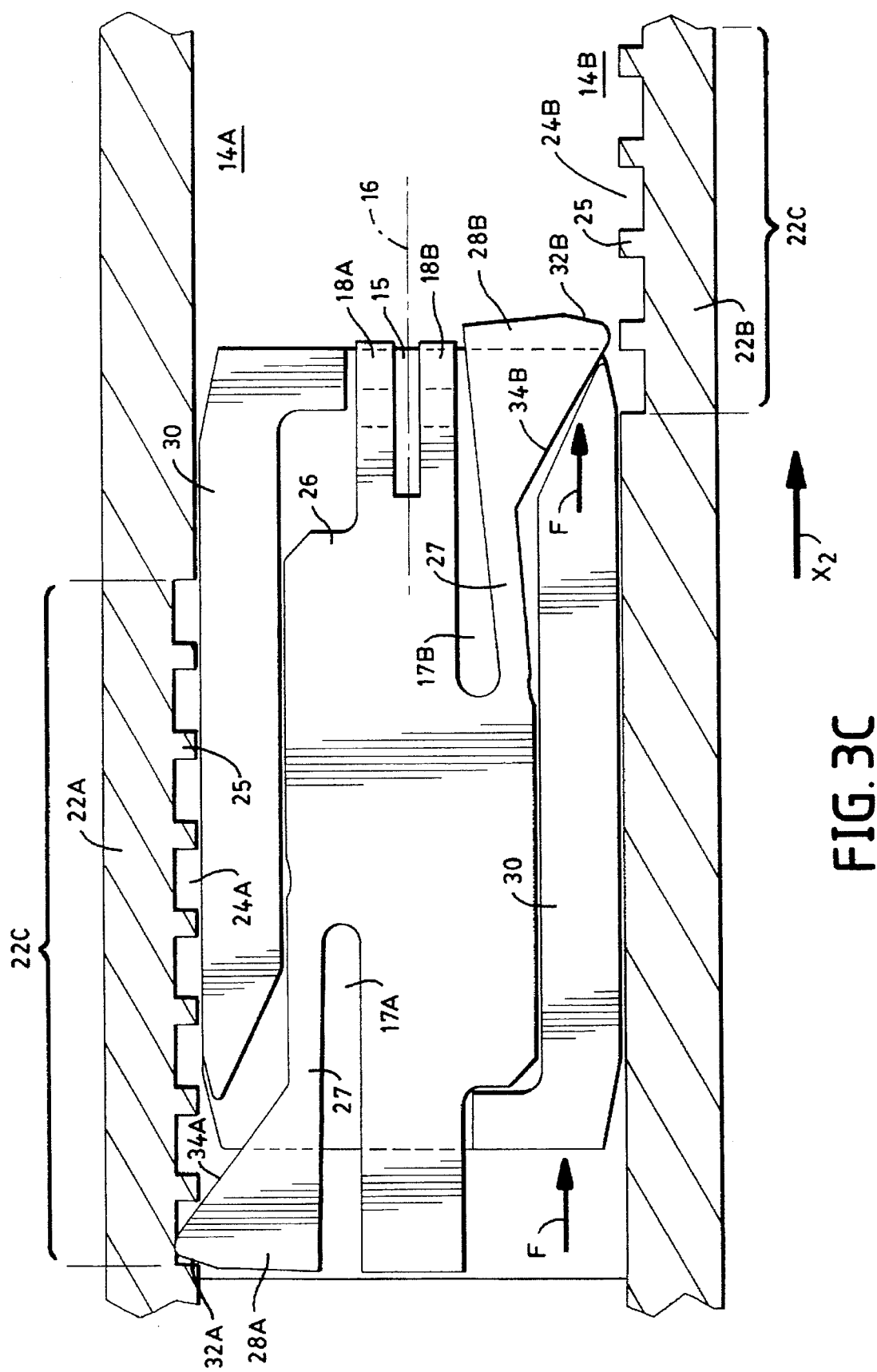
FIG. 3C is an enlarged detail cross-sectional view of the bi-directional positioning assembly shown FIG. 3A, in which force is applied to the control element in an axial direction X2 opposite to direction X1.

The bi-direction position control of the tool support assembly 10 is shown in FIG. 2B and in enlarged detail in FIGS. 3A–3C. The housing 12 defines an interior channel 14 which extends along an axis 16. A tool support element 18 is positioned within the channel 14. Element 18 is adapted for gripping a surgical tool or instrument such as a blade. The tool support element 18 is movable axially within the channel 14 in response to application of a force on a control element, discussed in more detail below. The tool support element 18 can comprise, for example, a pair of parallel fingers 18A, 18B defining an axial gap 15 therebetween, as shown in FIGS. 3A–3C. The surgical tool 10B can fit between the parallel fingers 18A, 18B and can be fixed thereto with a locking screw (not shown) or other fixation devices known in the art.

The bi-direction positioning assembly 20 couples the tool support element 18 and the housing 12. The positioning assembly 20 of the present embodiment includes two detent elements 22 which are fixed to the housing 12. The detent element 22 includes eight detents 24 exemplified by detents 24A, 24B in FIG. 3A, which extend transverse to the axis 16 and face the channel 14, as illustrated in FIGS. 3A–3C. The various detents are defined by radially extending members, exemplified by radial member 25 in FIGS. 3A–3C. In a preferred embodiment the detent 22 element is constructed as a linear array 22C of abutting surfaces. As will become more evident hereinafter, the detents 24 are configured selectively to engage and disengage with a corresponding lock arm 28.

The bi-directional positioning assembly 20 further includes at least one latch element 26 which is captively positioned within the channel 14 and which is selectively movable along the axis 16 within the channel 14. In the preferred embodiment, latch element 26 includes two lock arms 28 set apart by axial gaps 17. The lock arms 28 are coupled to the main portion of latch element 26 by flexures 27 and are shaped for selective engagement with the detents. As illustrated in FIGS. 3A–3C, the latch element 26 is between the lock arm 28 and the tool support element 18. As will become more evident in connection with a discussion of FIGS. 3B and 3C, axial gaps 17 permit the lock arm 28 to move transversely relative to the tool support element 18, thereby permitting the lock arm 28 to engage and disengage the detents 24.

The bi-directional positioning assembly 20 further includes a control element 30 which is captively positioned within the housing 12 and which is movable relative to the housing along the axis 16. The control element 30 is coupled to the external trigger 10C so that axial force F applied to the trigger 10C by the operator is directly transmitted to the control element 30.

The bi-directional positioning assembly 20 includes a first detent element 22A which is located on a first side 14A of the channel 14. Similarly, the positioning assembly 20 includes a second detent element 22B located on a second side 14B of the channel 14. The second side 14B of the channel is opposite the first side 14A of the channel with the respective detent elements 22A, 22B facing each other. Both the first and the second detent elements 22A, 22B include a linear array 22C of detents 24 extending along the axis 16 and facing the interior of the channel 14, as illustrated in FIGS. 3A–3C.

The latch element 26 includes first and second lock arms 28A, 28B. The first lock arm 28A is resiliently biasable toward one of the detents 24A and is shaped for selective engagement therewith. Similarly, the second lock arm 28B is also resiliently biasable toward one of the detents 24B and is shaped for selective engagement therewith. As illustrated in FIGS. 3A–3C, the lock arms 28A, 28B extend in opposite directions along axis 16 and have a shape which includes a generally leading edge 32 and a generally trailing edge 34.

The first lock arm 28A includes an element 32A which operates in response to the application of a force F to the tool support element 18 relative to the housing 12 in a first axial direction X1. The element 32A is adapted for interfering engagement with one of the radial members 25 of the first detent element 22A to prevent motion of the tool support element 18, and thus the tool 10B, relative to the housing 12 in the first axial direction X1. Similarly, the first lock arm 28A further includes an element 34A which operates in response to the application of a force F to the tool support element 18 relative to the housing 12 in a second axial direction X2, the directions X1 and X2 being in mutually opposing directions along axis 16. The element 34A operates to disengage lock arm 28A from the detents 24 of the first detent element 22A to permit motion of the tool support element 18 relative to the housing 12 in the second axial direction X2.

In like manner, the second lock arm 28B includes an element 32B which operates in response to application of a force F on the tool support element 18 relative to the housing 12 in the second axial direction X2. The element 32B is adapted for interfering engagement with one of the radial members 25 of the second detent element 22B to prevent motion of the tool support element 18 relative to the housing 12 in the second direction X2. Likewise, the second lock arm 28B also includes an element 34B which operates in response to application of a force F on the tool support element 18 relative to the housing 12 in the first axial direction X1. The element 34B is adapted for disengaging the lock arm 28B from detents 24B of the second detent element 22B to permit motion of the tool support element 18 relative to the housing 12 in the first axial direction X1.

FIGS. 3B and 3C illustrate movement of the lock arms 28A, 28B in response to application of axial force F. In FIG. 3B, application of axial force F in a direction X1 on the trigger element 10C (not shown) transmits axial force F to control element 30. Axial movement of the control element 30 in axial direction X1 causes the control element 30 to slidingly engage with surface 34A of the lock arm 28A. Sliding engagement of these two mating surfaces causes lock arm 28A to move in a transverse direction relative to the tool support element 18, thereby closing axial gap 17A and permitting transverse movement of the lock arm 28A and disengagement of the lock arm 28A from detent 24A. When lock arm 28A is no longer engaged with detent 24A, the tool support element 18 and the tool 10B affixed therein are free to move axially along axis 16. Note that during application of the force F in the direction X1, the opposing lock arm 28B also moves axially in the same direction. Trailing surface 34B of the lock arm 28B is adapted for sliding engagement over the detents 24B and radial members 25, thereby permitting the trailing lock arm 28B to ride over the detents 24B and radial members 25 without engaging therewith to prevent axial motion of the tool and tool support element 18. Thus, in response to a force F applied to the control element 30 relative to the housing 12 in a first direction X1 along the axis 16, the lock arms 28 disengage from detents 24, thereby permitting the tool support element 18 to move relative to the housing 12 in the first direction X1 along axis 16.

FIG. 3C illustrates the operation of the bi-direction control assembly when force is applied along the second axial direction X2. Application of a force F to the trigger element 10C (not shown) transmits the force to the control element 30. Application of force F to the control element 30 causes control element 30 to move axially in a direction X2 to engage with lock arm 28B at surface 34B. Axial gap 17B permits transverse movement of the lock arm 28B relative to the tool support element 18, thereby permitting the lock arm 28B to disengage from the detent 24B in response to application of force F against lock arm surface 34B. When lock arm 28B is no longer engaged with detent 24B, the tool support element 18 and the tool 10B affixed therein can move freely along axis 16 in the direction X2. Note that the opposing lock arm 28A has no force F applied to it and thus rides over detents 24A and radial members 25 in the direction X2 along the axis 16 in response to application of force F on control element 30 in the direction X2. Thus, in response to a force F applied to the control element 30 relative to the housing 12 in the second axial direction X2, the lock arms 28A, 28B disengage from the detents 24, thereby permitting the tool support element 18 to move relative to the housing 12 in the second axial direction X2.

The bi-directional position control of the present invention permits an operator to selectively position an instrument relative to an instrument housing and further permits the operator to lock the instrument in any of those selected positions. Application of axial force F to the control element 30 via trigger element 10C in a first axial direction X1 causes the lock arms 28 to disengage from the detents 24 and permits axial movement of the tool support element 18 in that direction. Similarly, application of axial force F in an opposite direction X2 on the control element 30 also disengages the lock arms 28 from the detents 24 and permits the tool support element 18 to move axially in that direction relative to the housing. Note that only force which is applied to the control element 30 can cause movement of the tool support element 18 relative to the housing 12. Application of force on any other element of the device, including the tool 10B itself, will not cause the lock arms 28 to disengage from the detents 24 to permit axial movement thereof as a result of the inventive arrangement of the lock arms 28 and detents 24. Thus, the bi-direction position control of the present invention has particular advantages with regard to safety and stability of the surgical instrument during operation. Finally, the bi-directional position control of the present invention can be easily controlled single-handedly by the application of axial force alone; it is unnecessary to apply transverse or rotational force to the trigger element 10C to lock the instrument in a selected position.

The invention may be embodied in other specific forms without departing from the spirit or essential characteristics thereof. The present embodiment are therefore to be considered in all respects as illustrative and not restrictive, the scope of the invention being indicated by the appended claims rather than by the foregoing description. All changes that come within the meaning and range of the equivalency of the claims are therefore intended to be embraced therein.

We claim:

1. A tool support assembly with a bi-directional position control, comprising:

A. a housing defining an interior channel extending along an axis,

B. a tool support element positioned within said channel and movable in said channel along said axis, and C. a bidirectional positioning assembly coupling said tool support element and said housing, including:

i. at least one detent element affixed to said housing, said detent element including at least one detent extending transverse to said axis and facing said channel, ii. a latch element captively positioned within said channel and selectively movable along said axis, said latch element including at least one lock arm resiliently biasable toward and for selectively engaging at least one of said detents, iii. a control element captively positioned within said housing and movable relative to said housing along said axis, wherein said latch element and said control element cooperate whereby:

a. in response to substantially no force F applied to said control element relative to said housing and when at least one of said lock arms is engaged with one of said detents, said tool support element is fixedly positioned relative to said housing, and b. in response to a force F applied to said housing in a first direction along said axis, said lock arms disengage said at least one of said detents and said tool support element moves relative to said housing in said first direction, wherein said latch element and said control element further cooperate whereby in response to a force F applied to said control element relative to said housing in a second direction along said axis, said second direction being opposite to said first direction, said lock arms disengage said detents and said tool support element moves relative to said housing in said second direction, and wherein said bidirectional positioning assembly includes a first detent element on a first side of said channel and a second detent element on a second side of said channel, said second side being opposite said first side, and each of said first and second detent elements including a linear array of detents extending along said axis and facing said channel, and wherein said latch element includes first and second lock arms, said first lock arm being resiliently biasable toward and for selectively engaging one of said detents of said first detent element, and said second lock arm being resiliently biasable toward and for selectively engaging one of said detents of said second detent element.

2. A tool support assembly according to claim 1 wherein said first lock arm includes:

means operative in response to force F applied to said tool support element relative to said housing in said first direction for interferingly engaging one of said detents of said first detent element to prevent motion of said tool support element relative to said housing in said first direction, and means operative in response to force F applied to said tool support element relative to said housing in said second direction for disengaging from said detents of said first detent element to permit motion of said tool support element relative to said housing in said second direction.

3. A tool support assembly according to claim 2 wherein said second lock arm includes:

means operative in response to force F applied to said tool support element relative to said housing in said second direction for interferingly engaging one of said detents of said second detent element to prevent motion of said tool support element relative to said housing in said second direction, and means operative in response to force F applied to said tool support element relative to said housing in said first direction for disengaging from said detents of said second detent element to permit motion of said tool support element relative to said housing in said first direction.

* * * * *